United States Patent [19]
Vegeto et al.

[11] Patent Number: 5,364,791
[45] Date of Patent: Nov. 15, 1994

[54] PROGESTERONE RECEPTOR HAVING C. TERMINAL HORMONE BINDING DOMAIN TRUNCATIONS

[76] Inventors: Elisabetta Vegeto, 7707 Eads Ave., LaJolla, Calif. 92037; Donald P. McDonnell, 10382 Rue Riviere Verte, San Diego, Calif. 92131; Bert W. O'Malley, 629 Ramblewood, Houston, Tex. 77079

[21] Appl. No.: 882,771

[22] Filed: May 14, 1992

[51] Int. Cl.$^5$ .................... C12N 15/00; C07H 17/00; G01N 33/53; C07K 13/00
[52] U.S. Cl. .................. 435/320.1; 536/23.1; 435/7.8; 530/350
[58] Field of Search ............ 530/350; 435/69.4, 240.1, 435/320.1, 7.1, 7.8; 536/23.1

[56] References Cited

U.S. PATENT DOCUMENTS 4,898,425 2/1990 Mundy ................................ 297/444
5,062,677 11/1991 Jay et al. ...................... 297/DIG. 4

FOREIGN PATENT DOCUMENTS 372516 5/1932 United Kingdom ................ 297/231

OTHER PUBLICATIONS

Meyer et al 1990 EMBO J 9:3923.
Berry et al 1990 EMBO J 9:2811.
Dobson et al. 1989 J. Biol. Chem 264(7) 4207–4211.
M. K. Bagchi et al., "Identification of a functional intermediate in receptor activation in progesterone–dependent cell–free transcription", Nature, 1990;345:547–550.
B. Benhamou et al., "A Single Amino Acid That Determines the Sensitivity of Progesterone Receptors to RU846", Science, 1991;255:206–209.
K. Horwitz, "The Antiprogestin RU38 486: Receptor–Mediated Progestin Versus Antiprogestin Actions Screened in Estrogen–Insensitive T47Dco Human Breast Cancer Cells", Endocrinology, 1986;vol. 116, No. 6, pp. 2236–2245.
K. Christensen et al., "Characterization and Functional Properties of the A and B Forms of Human Progesterone Receptors Synthesized in a Baculovirus System", Molecular Endocrinology, 1991; vol. 5, No. 11, pp. 1755–1770.
M. K. Bagchi et al., "Steroid Hormone–Dependant Interaction of Human Progesterone Receptor with its Target Enhancer Element", Molecular Endocrinology; 1988; vol. 2, No. 12, pp. 1221–1229.
M. A. Carson et al., "Structure–Function Properties of the Chicken Progesterone Receptor A Synthesized from Complementary Deoxyribonucleic Acid", Molecular Endocrinology; 1987; vol. 1, No. 11, pp. 791–801.
R. Evans, "The Steroid and Thyroid Hormone Receptor Superfamily", Science; 1988; 240:889–894.
O. Conneely et al., "The Chicken Progesterone Receptor A and B Isoforms Are Products of an Alternate Translation Initiation Event", Journal of Biological Chemistry, 1989, vol. 264, No. 24, pp. 14062–14064.
O. Conneely et al., "The A and B Forms of the Chicken Progesterone Receptor Arise by Alternate Initiation of Translation of a Unique mRNA", Biochemical and Biophysical Research Communications, 1987, vol. 149, No. 2, pp. 493–501.

(List continued on next page.)

Primary Examiner—Robert J. Hill, Jr.
Assistant Examiner—K. Cochrane Carlson
Attorney, Agent, or Firm—Fulbright & Jaworski

[57] ABSTRACT

The present invention provides mutant proteins of steroid hormone receptors. These mutant proteins are useful in methods of distinguishing a steroid hormone receptor antagonist from a steroid hormone receptor agonist. The present invention also provides plasmids containing mutated steroid hormone receptor proteins and cells transfected with those plasmids. In addition, the present invention provides methods for determining whether a compound is a steroid hormone receptor antagonist or agonist. Also, the present invention provides methods of determining endogenous ligands for steroid hormone receptors.

17 Claims, 9 Drawing Sheets

OTHER PUBLICATIONS

J. Elliston et al., "Hormone Activations of Baculovirus Expressed Progesterone Receptors", 1992, vol. 267, No. 8, pp. 5193–5198.

H. Gronemeyer et al., "Progestin Receptors:Isoforms and Anti-hormone Action", J. Steroid Biochem. Molec. Biol., 1991; vol. 40, No. 1, pp. 271–278.

H. Gronemeyer et al., "The chicken progesterone receptor: suquence, expression and functional analysis", The EMBO Journal, vol. 6, No. 13, pp. 3985–3994, 1987.

L. Shemshedini, et al., "In Vitro Activity of the Transcription Activation Functions of the Progesterone Receptor", Journal of Biological Chemistry, vol. 267, No. 3, pp. 1834–1839, 1992.

G. Takimoto et al, "Hormone-induced progesterone receptor phosphorylation consists of sequential DNA-independent and DNA-dependent stages: Analysis with zinc finger mutants and the progesterone antagonist 7K98299", Proc. Natl. Acad. Sci. USA, vol. 89, pp. 3050–3054, 1992.

M. K. Bagchi et al., "Ligand and DNA-dependent phosphorylation of human progesterone receptor in vitro", Proc. Natl. Acad. Sci. USA, vol. 89, pp. 2664–2668, 1992.

E. Baulieu, "Steroid Hormone Antagonists at the Receptor Level: A Role for the Heat-Shock Protein MW 90,000 (hsp 90)", Journal of Cellular Biochemistry, 35:161–174 1987.

E. Baulieu, "Contragestion and Other Clinical Applications of RU 486, an Antiprogesterone at the Receptor", Science, vol. 24, pp. 1351–1357, 1989.

C. Chao et al., "Ionic and Ligand-specific Effects on the DNA Binding of Progesterone Receptor Bound to the Synthetic Progestin R5020 and the Antiprogestin RU486", Cancer Research, 51:3938–3945, 1991.

L. Denner et al., "Regulation of Progesterone Receptor-Medicated Transcription by Phosphorylation", Science, 250:1740–1743, 1990.

M. Beato, "Gene Regulation by Steroid Hormones", Cell. vol. 56, 335–344, 1989.

D. El-Ashry et al., "Human Progesterone Receptor Complexed with the Antagonist RU 486 Binds to Hormone Response Elements in a Structurally Altered Form", Molecular Endocrinology, vol. 3, No. 10, pp. 1545–1558, 1989.

S. Fawell et al., "Characterization and Colocalization of Steroid Binding and Dimerization Activities in the Mouse Estrogen Receptor", Cell. vol. 60, 953–962, 1990.

V. Giguere et al., "Functional Domains of the Human Glucocorticoid Receptor", Cell, 46:645–652, 1986.

A. Groyer et al., "Antiglucocorticosteroid effects suggest why steroidhormone is required for receptors to bind DNA in vivo but not in vitro", Nature, 328:624–626, 1987.

A. Guiochon-Mantel et al., "Receptors bound to antiprogestin from abortive complexes with hormone responsive elements", Nature, 356:695–698, 1988.

L. Klein-Hitpass et al., "The Progesterone Receptor Stimulates Cell-Free Transcription by Enhancing the Formation of a Stable Preinitiation Complex", Cell, 60:247–257, 1990.

P. Mak et al., Expression of Functional Chicken Oviduct Progesterone Receptors in Yeast (Saccharomyces cerevisiae), The Journal of Biological Chemistry, vol. 264, No. 36, pp. 21613–21618, 1989.

M. E. Meyer et al., "Agonistic and antagonistic activities of RU486 on the functions of the human progesterone receptor", The EMBO Journal, vol. 9, No. 12, pp. 3923–3932, 1990.

D. McDonnell et al., "Functional Domains of the Human Vitamin D3 Receptor Regulate Osteoclacin Gene Expression", Molecular Endocrinology, vol. 3, No. 4, pp.635–644, 1989.

M. L. Privalsky et al., "The Viral erbA Oncogene Protein, a Constitutive in Animal Cells, Is a Hormone-Regulated Repressor Activator in Yeast", Cell, 63:1277–1286, 1990.

M. K. Bagchi et al., "Progesterone Enhances Target Gene Transcription by Receptor Free of Heat Shock (List continued on next page.)

OTHER PUBLICATIONS

Proteins hsp90, hsp56, and hsp70", Molecular and Cellular Biology, pp. 4998–5004, 1991.

M. T. Bocquel et al., "The contribution of the N- and C-terminal regions of steroid receptors to activation of transcription is both receptor and cell-specific", Nucleic Acids Research, vol. 17, No. 7, pp. 2581–2595, 1989.

M. A. Carson-Jurica et al., "Steroid Receptor Family: Structure and Functions", Endocrine Reviews, vol. 11, No. 2, pp. 201–220, 1990.

A. Cato et al., "The hormone regulatory element of mouse mammary tumour virus mediates progesterone induction", The EMBO Journal, vol. 5, No. 9, pp. 2237–2240, 1986.

D. McDonnell et al., "Reconstruction of the Vitamin D-Responsive Osteocalcin Transcription Unit in Saccharomyces cerevisiae", Molecular and Cellular Biology, vol. 9, No. 8, pp. 3517–3523, 1989.

D. McDonnell et al., "In Situ Distinction between Steroid Receptor Binding and Transactivation at a Target Gene", Molecular and Cellular Biology, vol. 11, No. 9, pp. 4350–4355, 1991.

M. Misrahi et al., "Complete Amino Acid Sequence of the Human Progesterone Receptor Deduced from Cloned cDNA", Biochemical and Biophysical Research Communications, vol. 143, No. 2, pp. 740–748, 1987.

B

DNA sequence:

```
        2636                                                        
WT   ..AAC TTG CAT GAT CTT GTC AAA CAA CTT CAT CTG TAC TGC TTG..
UP-1 ..AAT TGC ATG ATC TTG TCA AAC AAC TTC ATC TGT ACT GCT TGA
```

Protein sequence:

```
       879                                                    891
WT   ..Asn Leu His Asp Leu Val Lys Gln Leu His Leu Tyr Cys Leu..
                                     *   *
UP-1 ..Asn Cys Met Ile Leu Ser Asn Asn Phe Ile Cys Thr Ala
``` wild type

| DNA | hormone |

| hPR Constructs | | Transcriptional Activity (Miller Units) | | | Specific Binding (nM) | |
| --- | --- | --- | --- | --- | --- | --- |
| | | − | P | RU | P | RU |
| YEphPR-B (933) | ☐ | 86 | 6200 | 586 | 1.0 | 1.3 |
| UP-1 | ☐ | 286 | 466 | 8050 | 0.02 | 1.6 |
| YEphPR-B879 | ☐ | 166 | 242 | 5900 | 0.04 | 1.8 |
| YEphPR-B891 | ☐ | 243 | 226 | 6175 | 0.03 | 1.6 |

Figure 4

PROGESTERONE RECEPTOR HAVING C. TERMINAL HORMONE BINDING DOMAIN TRUNCATIONS

BACKGROUND OF THE INVENTION

1. Field of the Invention

The present invention relates generally to the fields of molecular endocrinology and receptor pharmacology. More specifically, the present invention relates to a novel in vivo method for the identification of steroid hormone receptor agonists and antagonists.

2. Description of the Related Art

The ovarian hormones, estrogen and progesterone, are responsible, in part, for the regulation of the complex cellular events associated with differentiation, growth and functioning of female reproductive tissues. These hormones also play important roles in development and progression of malignancies of the reproductive endocrine system.

The biological activity of steroid hormones is mediated directly by a hormone and tissue-specific intracellular receptor. The physiologically inactive form of the receptor may exist as an oligomeric complex with proteins, such as heat-shock protein (hsp) 90, hsp70 and hsp56. Upon binding its cognate ligand, the receptor changes conformation and dissociates from the inhibitory heteroligomeric complex. Subsequent dimerization allows the receptor to bind to specific DNA sites in the regulatory region of target gene promotors. Following binding of the receptor to DNA, the hormone is responsible for mediating a second function that allows the receptor to interact specifically with the transcription apparatus. Displacement of additional inhibitory proteins and DNA-dependent phosphorylation may constitute the final steps in this activation pathway.

Cloning of several members of the steroid receptor superfamily has facilitated the reconstitution of hormone-dependent transcription in heterologous cell systems. Subsequently, in vivo and in vitro studies with mutant and chimeric receptors have demonstrated that steroid hormone receptors are modular proteins organized into structurally and functionally defined domains. A well defined 66 amino acid DNA binding domain (DBD) has been identified and studied in detail, using both genetic and biochemical approaches. The hormone binding domain (HBD), located in the carboxyl-terminal half of the receptor, consists of about 300 amino acids. It has not been amenable to detailed site-directed mutagenesis, since this domain appears to fold into a complex tertiary structure, creating a specific hydrophobic pocket which surrounds the effector molecule. This feature creates difficulty in distinguishing among amino acid residues that affect the overall structure of this domain from those involved in a direct contact with the ligand. The HBD also contains sequences responsible for receptor dimerization, hsp interactions and one of the two transactivation sequences of the receptor.

Although antiprogestins are presently used for pregnancy termination and in the treatment of hormone-dependent breast cancer, little is known about their mechanism of action. Nevertheless, certain insights to the role of ligand in progesterone receptor activation have come from the study of antihormones. Upon binding most antihormones, the receptor is driven to steroid responsive elements (SREs) within the regulatory regions of target genes. The affinity of antagonist activated receptor for DNA is indistinguishable from that of agonist-bound receptor. Nevertheless, in the presence of the antagonist, the receptor cannot activate transcription efficiently. A plausible explanation for this observation is that antihormones and hormones alter conformation differently. Agonists may induce conformational changes which expose the receptor transcription activation domain, whereas antagonists may promote DNA binding but induce a conformation which is transcriptionally silent.

Steroid receptors and other mammalian transcription regulators can function in yeast. This fact, coupled with the ease of genetic manipulation of yeast make it a useful system to study the mechanism of steroid hormone action.

A long felt need and desire in this art would be met by the development of methods to identify steroid hormone receptors agonists and antagonists. The development of such a method will facilitate the identification of novel therapeutic pharmaceuticals.

SUMMARY OF THE INVENTION

In one embodiment of the present invention, there is provided a mutated steroid hormone receptor protein. This mutated steroid hormone receptor protein is capable of distinguishing a steroid hormone receptor antagonist from a steroid hormone receptor agonist.

In another embodiment of the present invention, there is provided a plasmid containing a mutated steroid hormone receptor protein. The plasmid of the present invention is common when transfected into a cell, useful in determining the relative antagonist or agonist activity of a compound for a steroid hormone receptor.

In yet another embodiment of the present invention, there is provided a transfected cell containing a plasmid in which DNA encoding a mutated or steroid hormone receptor protein has been inserted. The transfected cells of the present invention are useful in methods of determining the activity of a compound for a steroid hormone receptor.

And still yet another embodiment of the present invention, there are provided methods of determining whether a compound has activity as an agonist or antagonist as a steroid hormone receptor. These methods comprise initially contacting the compound of interest with the transfected cells of the present invention. Subsequently, transcription levels induced by the compound are measured and the relative agonist or antagonist activity of the steroid hormone receptors is determined.

And still yet other embodiments of the present invention, there is provided a method of determining an endogenous ligand for a steroid hormone receptor. This method comprises contacting a compound with the transfected cells of the present invention. Subsequently transcription levels induced by the compound are measured. The present invention also provides for endogenous ligand for steroid hormone receptors. These endogenous ligands are capable of stimulating transcription when in the presence of the transfected cells of the present invention.

BRIEF DESCRIPTION OF THE DRAWINGS

FIGS. 2A and 2B illustrate the functional and structural characterization of the UP-1 mutant.

FIG. 4 shows the transcriptional activity and hormone binding analysis of wild type and mutant human progesterone receptor constructs.

DETAILED DESCRIPTION OF THE INVENTION

Definitions

Figure 1:
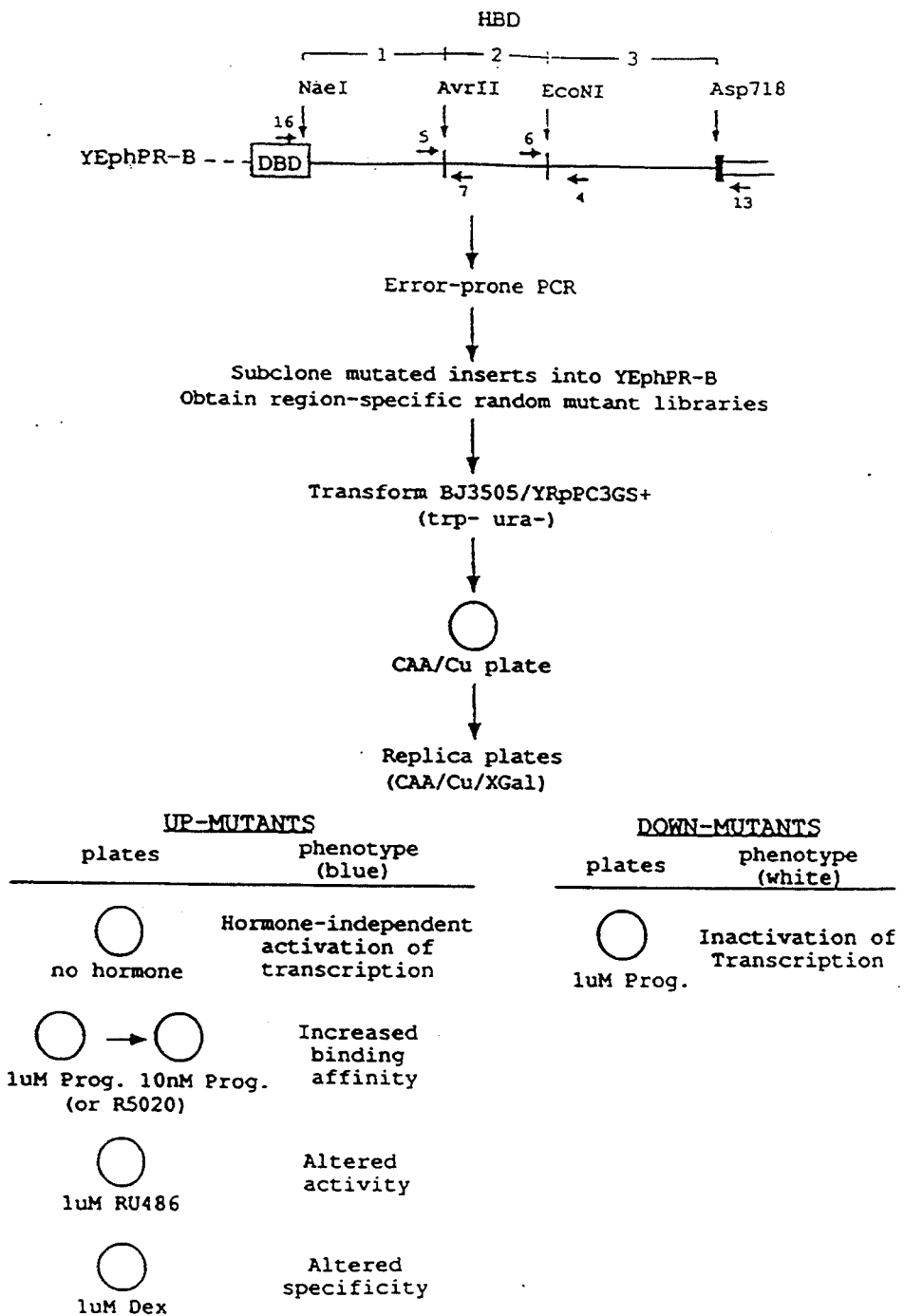
FIG. 1 shows the mutagenesis and screening strategy used in the present experiments.

"Agonist" is a compound which interacts with the steroid hormone receptor to promote a transcriptional response. For example estrogen is an agonist for the estrogen receptor and compounds which mimic estrogen would be defined as steroid hormone receptor agonists.

"Antagonist" is a compound which interacts with or binds to a steroid hormone receptor and blocks the activity of a receptor agonist.

"Estrogen response element" is a synthetic or naturally occurring DNA sequence which, when placed into a heterologous promotor can confer estrogen responsiveness to that promotor in the presence of estrogen activated estrogen receptor.

"Mutant" refers to an alteration of the primary sequence of the estrogen receptor such that it differs from the wild type or naturally occurring sequence.

"Plasmid activity" is a phenotypic consequence that relates specifically to introduction of a plasmid into an assay system.

"Transcriptional activity" is a relative measure of the degree of RNA polymerase activity at a particular promotor.

"Receptor activity" is a phenotypic consequence that relates specifically to introduction of a receptor into an assay system.

"Anti-hormone" is a receptor antagonist. A compound that is opposite in activities to a hormone.

"Transfected/Transfection" is a term describing the process of directly introducing DNA into a mammalian cell.

"Transformed/Transformation" is the result of introducing DNA into a cell where the presence of the DNA genotypically and phenotypically alters a cell in a heritable manner.

"Orphan receptors" is a designation given to a series of cloned receptors whose primary sequence is closely related to the steroid hormone receptors but for which no ligand has been described.

"A and B forms of the progesterone receptor" are two distinct forms of the progesterone receptor that are derived from the same gene. The process for generation of the products may be alternate initiation of transcription, splicing differences or may relate to the promotor structure.

"Expression vector" is a DNA plasmid that contains all the information necessary to produce a recombinant protein in a heterologous cell.

"Null mutation" is a genetic lesion to a gene locus that totally inactivates the gene product.

"Steroid hormone receptor superfamily" is a classification of a group of proteins, some of which are known steroid receptors whose primary sequence suggests that they are related to each other. Examples include the estrogen, progesterone, androgen, thyroid hormone and mineralocorticoid receptors.

The present invention provides mutant proteins of steroid hormone receptors. These mutated steroid hormone receptor proteins are useful in methods of distinguishing a steroid hormone receptor antagonist from a steroid hormone receptor agonist.

Steroid hormone receptors which may be mutated are any of those receptors which comprise the steroid hormone receptor superfamily. Representative examples of such receptors include the estrogen, progesterone, glucocorticoid-$\alpha$, glucocorticoid-$\beta$, mineralocorticoid, androgen, thyroid hormone, retinoic acid, retinoid X, and Vitamin D3 receptors.

The mutant steroid hormone receptor protein of the present invention is mutated by deletion of amino acids on the carboxy terminal end of the protein. Generally, a deletion of from about 1 to about 120 amino acids from the carboxy terminal end of the protein provides a mutant useful in the present invention. A person having ordinary skill in this art will recognize, however, that a shorter deletion of carboxy terminal amino acids will be necessary to create useful mutants of certain steroid hormone receptor proteins. For example, a mutant of the progesterone receptor protein will contain a carboxy terminal amino acid deletion of from about 1 to about 60 amino acids.

The present invention also provides plasmids containing mutated steroid hormone receptor proteins. Plasmids of the present invention may contain mutant proteins of any of the hormones in the steroid hormone receptor superfamily.

The present invention also provides transfected cells containing plasmids having mutated steroid hormone receptor proteins inserted therein. Useful cells for transfection include yeast, mammalian and insect cells. The present invention also provides stable cell lines transformed with plasmids of the present invention.

The plasmids and transfected cells of the present invention are useful in methods of determining whether a compound has antagonist or agonist activity at a steroid hormone receptor. This method comprises contacting a compound of interest with a transfected cell of the present invention. If the compound induces transcription, it has a steroid hormone receptor antagonist. If no transcription is induced, the compound may be a steroid hormone receptor agonist.

The present invention also provides a method of determining an endogenous ligand for a steroid hormone receptor protein. This method comprises initially contacting a compound with a transfected cell of the present invention. Subsequently, the transcription level induced by the compound is measured. In addition, the present invention provides endogenous ligands for steroid hormone receptor proteins. An endogenous ligand for a steroid hormone receptor protein is capable of stimulating transcription when in the presence of a transfected cell of the present invention.

EXAMPLE 1

The homogenization buffer for hormone binding assays contained 10 mM Tris-HCl, 1.5 mM EDTA, 1 mM dithiothreitol, pH 7.4 (TESH buffer). The homogenization buffer for Western analysis of receptor contained 10 mM Tris-HC l, 2 mM EDTA, 45 mM dithiothreitol, 10% glycerol and 300 mM NaCl (TEDG+salts).

Yeast strain

The *Saccharomyces cerevisiae* strain B13505 (Matu1 pep4:HIS3, Prb1-A1.6R, his3, lys2-208, trpl-l0l, ura3-52, gal2, (CUP1)) was used (Yeast Genetic Stock Center, Berkeley, Calif.). All yeast transformations were carried out following the lithium acetate transformation protocol (Ito, et al., *J. Bacteriol.* 153:163–168, 1983).

The PCR reactions were carried out using YEphPR-B DNA template (a YEp52AGSA-derived yeast expression plasmid containing the cDNA of hPR form-B (Misrahi, et al., *Biochem. Bioph. Res. Comm.* 143:740–748, 1987) inserted downstream of the yeast methallothionein-CUP1 promotor) and using three different sets of primers. In order to decrease the fidelity of the second strand polymerization reaction, buffer conditions of 1.5 mM MgCl2, 0.1 mM dNTPs and pH 8.2 were used. About 2000 primary transformants were obtained from each region-specific library.

EXAMPLE 2

Yeast Mutant Screening

Colonies of each library of hPR molecules mutated in specific subregions were pooled, large amounts of DNA were prepared and used to transform yeast cells carrying the reporter plasmid YRpPC3GS+, which contains two GR IE PRE elements upstream of the CYC1 promotor linked to the Lac-Z gene of *E. coli* (Mak, et al., *J. Biol. Chem.* 265:20085–20086, 1989). The transformed cells were plated on 1.5% agar plates containing 2% glucose, 0.5% casamino acids (5% stock solution of casamino acids is always autoclaved before use to destroy tryptophan), 6.7 g/l yeast nitrogen base (without amino acids) and 100 μM CuSO4 (CAA/Cu plates) and grown for 2 days at 30° C. These colonies were then replica-plated on CAA/Cu plates containing 0.16 g/l of 5-bromo-4-chloro-3-indolyl-β-D-galactoside (X-Gal, an indicator of β-galactosidase activity) with or without the hormones as indicated in FIG. 1 and allowed to grow for one day at 30° C., then two days at room temperature in the dark.

EXAMPLE 3

Growth of Yeast Culture for In Vitro Assay

*Saccharomyces cerevisiae* cells containing YEphPRB and the reporter plasmid were grown overnight at 30° C. in minimal media containing 2% glucose. The cells were subcultured in fresh medium and allowed to grow until early mid-log phase (O.D.$_{600\ nm}$=1.0). Induction of receptor was initiated by the addition of 100 μM copper sulfate to the culture. Cells were harvested by centrifugation at 1,500 xg for 10 minutes and resuspended in the appropriate buffer. This and all subsequent steps of analysis of the yeast extracts were done at 4° C.

EXAMPLE 4

Transcription Assay

Yeast cells containing the reporter and expression plasmids were grown overnight as described above in Example 3 in the presence of 100 μM copper sulfate. When the cell density reached O.D.$_{600\ nm}$=1.0, hormones were added to the cultures. After a 4 hour incubation, yeast extracts were prepared and assayed for β-galactosidase activity as described previously (Miller, *J. M. Miller ed.*, 352–355, 1972).

Generally, reporters useful in the present invention are any which allow for appropriate measurement of transcription levels. Preferable reporter systems have been described in copending patent application, U.S. Ser. No. 07/639,506.

EXAMPLE 5

Western Immunoblotting

Yeast cells were grown as described in Example 4 for the transcription assay. Yeast extracts for Western blot analysis were prepared by resuspending the cell pellet in TEDG+salts. The cell suspension was mixed with an equal volume of glass beads and disrupted by vortexing in a microcentrifuge tube. The homogenate was centrifuged at 12,000×g for 10 minutes. The supernatant was collected and the protein concentration was estimated using bovine serum albumin as standard. Yeast extracts were resolved on a 0.1% sodium dodecyl sulfate-7% polyacrylamide gel and transferred to Immobilon membrane as described previously (McDonnell, et al., *Mol. Cell. Biol.* 9:3517–3523, 1989). Solid phase radioimmunoassay was performed using a monoclonal antibody (JZB39) directed against the N-terminal domain of A and B forms of hPR.

EXAMPLE 6

Hormone Binding Competition Assays

Induction of PR synthesis was initiated by the addition of 100 μM CuSO4 to the culture and incubation was continued for 6 hours. The cell pellet was resuspended in TESH buffer containing 1 μg/ml leupeptin, 10 μg/ml PMSF and 10 μg/ml pepstatin. The cell suspension was mixed with an equal volume of glass beads (0.5 mm; B. Braun Instruments) and disrupted by vortexing in a microcentrifuge tube. The homogenate was centrifuged at 12,000×g for 10 minutes and the supernatant was further centrifuged at 100,000×g for 30 minutes to obtain a cytosol fraction. Diluted yeast extracts (200 μl) containing 100 μg of total protein were incubated overnight at 4° C. with [$^3$H]ligand in the absence (total binding) or presence (non-specific binding) of a 100-fold excess of unlabelled ligand. Bound and free steroids were separated by addition of 500 μl of dextran-coated charcoal suspension (0.5% Norit A, 0.05% dextran, 10 mM Tris HCl, pH 7.4 and 1 mM EDTA). Specific binding was determined by subtracting nonspecific from total binding. Scatchard analysis was carried out as described previously by Mak, et al., *J. Biol. Chem.* 264:21613:21618.

EXAMPLE 7

Site-directed Mutagenesis

Mutants YEphPR-B879 and YEphPR-B891 were prepared following the procedure described by Dobson, et al., *J. Biol. Chem.* 264:4207–4211 (1989). C1236 cells were infected with mpPR90 (an M13 plasmid containing hPR cDNA). The resulting uridine-containing single-stranded DNA was annealed to 20-mer oligonucleotides containing a TGA stop codon corresponding to amino acids 880 and 892, respectively.

EXAMPLE 8

Construction of Mammalian Expression Vectors

The mammalian expression vector phPR-B contains the SV40 enhancer sequence upstream of the human growth hormone promotor linked to the hPR-B cDNA. This vector was digested with SalI and EcoRI. The 6.1 kb fragment (containing the 21 vector sequences and the 5'-1.5 kb of the hPR) was gel-purified and ligated to the 2.1 kb fragment of YEphPR-B891 (containing the 3'-end of the receptor) previously cut with SalI and EcoRI. The resulting plasmid, phPR-B891, encodes a 42 amino acid truncated version of hPR form B.

EXAMPLE 9

Mammalian Cell Transient Transfections and CAT-Assays

Five μg of chloramphenicol acetyltransferase (CAT) reporter plasmid, containing two copies of a PRE/-GRE from the tyrosine amino transferase gene linked to the thymidine kinase promotor (PRETKCAT), were used in transient cotransfection experiments together with 5 μg of wild type or mutant receptor DNAs. Transient cotransfections and CAT-assays were performed as described by Tsai, et al., *Cell* 57:443–448 (1989).

EXAMPLE 10

Mutagenesis of the Hormone Binding Domain of hPR-B

In order to characterize amino acids within the hPR HBD which are critical for ligand binding and hormone-dependent transactivation, libraries of mutated hPR molecules were created and the mutants introduced into a reconstituted progesterone-responsive transcription system in yeast. This system allowed the screening of large numbers of mutant clones and the direct, visual identification of phenotypes.

Unique restriction sites for NaeI, AvrII and EcoNI were created in the cDNA of hPR, obtaining three cassettes of 396, 209 and 400 nucleotides (regions 1, 2 and 3, respectively). For PCR mutagenesis three sets of primers (16+7 for region 1, 5+4 for region 2 and 6+13 for region 3) were used in the polymerization reaction using YEphPR-B as DNA template. The fragments obtained after PCR were digested with the appropriate enzymes, gel-purified and ligated into the parental plasmid YEphPR-B. Ligation mixes were used to transform bacterial cells and to obtain libraries of hPR molecules randomly point-mutated in the HBD. 5 μg of DNA were used from each library to transform yeast cells carrying the reporter plasmid YRpPC3GS+ and transformants were selected for tryptophan and uracil auxotrophy on CAA plates containing 100 μM CuSO$_4$. These were then replicated on CAA plates containing the hormones. The screening for "up-mutations" allowed identification of receptor mutants with hormone-independent transcriptional activity, or increased affinity for the ligand (these clones should remain blue when grown with 100-fold less hormone), or with an altered response to RU486 or a glucocorticoid analogue. In the "down-mutation" screening, receptor mutants that were transcriptionally inactive in the presence of the ligand were detected.

Because of the nature of the method used to generate the mutated DNA templates, it was necessary, firstly, to determine the quality of the libraries obtained. This was assessed by estimating the number of null-mutations generated by mutagenesis. We estimated the frequency of occurrence of transcriptionally inactive receptors (white colonies) compared to the total number of colonies. This frequency was about 7%.

The primary transformants were replica-plated onto plates containing the antiprogestin RU486. The wild type receptor is not activated by this hormone (FIG. 1). Using this screening strategy, a single colony was identified that displayed considerable transcriptional activity in response to the antihormone. Interestingly, the same colony did not display transcriptional activity when replica-plated in the presence of progesterone. The colony was purified and the phenotype was confirmed. Eviction of the expression vector from the clone, followed by reintroduction of the unmutated receptor, demonstrated that the phenotype was indeed related to the expression vector and was not the result of a secondary mutation. In addition, the mutated plasmid called UP-1, was rescued from yeast by passage through *E.coli* (as described in Ward, *Nucl. Acids Res.* 18:5319 (1990) and purified. This DNA was then reintroduced into yeast that contained only the reporter plasmid. As expected, the mutant phenotype was stable and related directly to the receptor expression plasmid.

EXAMPLE 11

Characterization of the UP-1 Mutant

The plate assays used to identify the receptor mutants are qualitative in nature. To further characterize the properties of UP-1, the activity of the receptor mutants was compared with that of the wild type receptor in a transcription assay. In this method, yeast cells transformed with either the wild type or the mutant receptor and a progesterone responsive reporter were grown overnight in the presence of 100 μM CuSO$_4$. When the cells had reached an O.D.$_{600 nm}$ of 1.0, they were supplemented with progesterone or RU486 and harvested by centrifugation after four hours. The β-galactosidase activity in the cell cytosol was then measured.

Figure 2A:
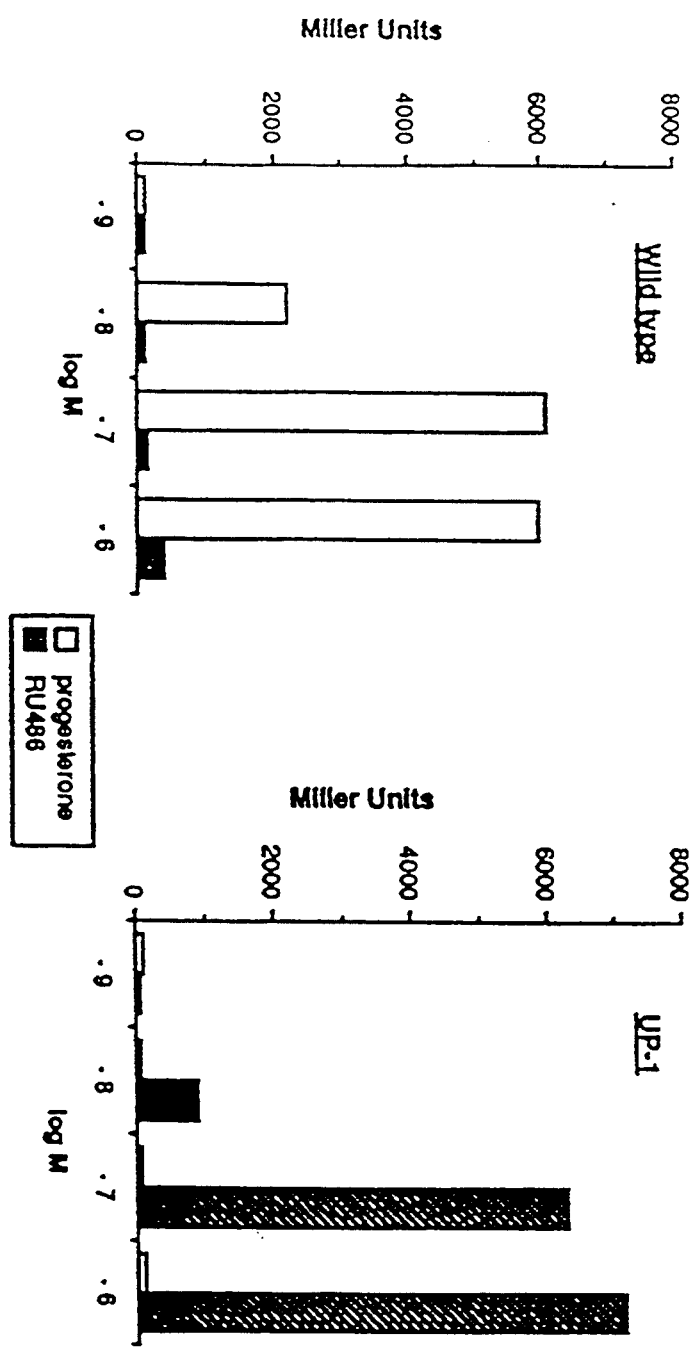

With reference to FIG. 2, panel (A), when assayed with the wild type receptor, 1 μM RU486 is a weak inducer of transcription, whereas progesterone caused a greater than 60-fold induction of transcription at 1 μM. However, this situation was reversed when the mutant was analyzed. In this case, RU486 was an extremely potent activator, whereas progesterone was ineffective. Interestingly, the activity achieved by the mutant in the presence of RU486 was of the same order of magnitude as that of the wild type assayed in the presence of progesterone. This reversal in specificity clearly indicates that the mechanism by which these ligands interact with the receptor is basically different.

FIG. 2 shows the DNA and amino acid sequences of the wild type and mutant DNAs. The cytosine at position 2636 was missing in the mutant DNA, therefore, a shifted reading frame was created and a stop codon was generated 36 nucleotides downstream of the C-2636 deletion. A schematic structure of the wild type and UP-1 receptors is also presented with a depiction of the 12 C-terminal amino acids unique to the mutant receptor. Conserved and structurally similar amino acids are marked by an apostrophe or asterisk, respectively.

DNA sequence analysis of UP-1 identified a single nucleotide deletion at base 2636 (FIG. 2B). This mutation results in a shift of the reading frame which generates a stop codon 36 nucleotides downstream. As a result, the wild type receptor is truncated by 54 authentic amino acids and 12 novel amino acids are added at the C-terminus.

EXAMPLE 12

Western Analysis of the Mutant Human Progesterone Receptor

Figure 3:
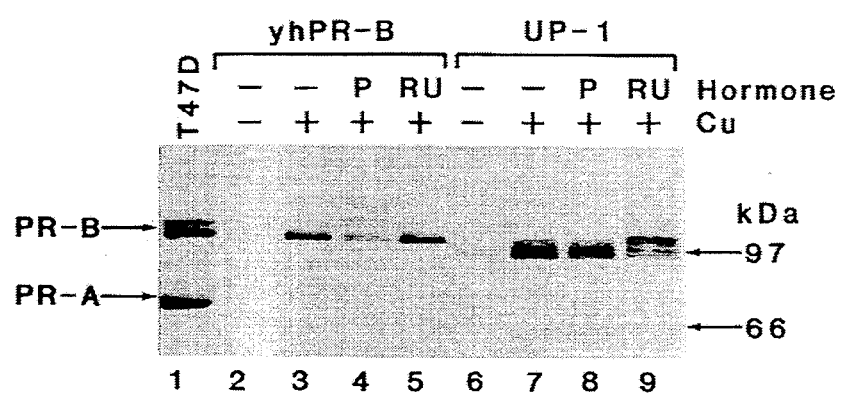
FIG. 3 shows a western analysis of the mutant human progesterone receptor.

FIG. 3 shows a western analysis of mutant hPR. Yeast cells carrying the reporter plasmid and wild type (ypPR-B or mutant (UP-1) hPR were grown overnight in CAA medium with (lanes 3 to 5 and 7 to 9) or without (lanes 2 and 6) 100 $\mu$M CuSO$_4$. 1 $\mu$M progesterone or 1 $\mu$M RU486 were added as indicated and cells were grown for another 4 hours. Yeast extracts were prepared as described above. 50 $\mu$g of protein extract were run on a 0.1% SDS-7% polyacrylamide gel. 50 $\mu$g of a T47D nuclear extract containing the A and B forms of hPR were also loaded (lane 1) as a positive control. The positions of molecular weight markers are indicated.

A Western immunoblot analysis of UP-1 and wild type receptors was performed in order to verify that the mutant receptor was synthesized as predicted from its DNA sequence and to eliminate the possibility that some major degradation products were responsible for the mutant phenotype. As shown in FIG. 3, the mutant receptor migrated faster in the gel, confirming the molecular weight predicted by DNA sequencing. The wild type receptor (yhPR-B) ran as a 114 kDa protein, while the mutant receptor was 5 kDa smaller (compare lanes 2 and 3 with 6 and 7). The addition of 100 $\mu$M CuSO$_4$ to the cell cultures increased synthesis of both the wild type and mutant hPR to the same extent. No major degradation products were detected. In the presence of progesterone and RU486, yhPR-B bands were upshifted due to hormone-induced phosphorylation of the receptor. In contrast, RU486 induced upshifting of wild type PR to a lesser extent (lanes 4 and 5). For the UP-1 mutant this hormone-dependent upshifting was seen upon treatment with RU486 (lanes 8 and 9). Thus, the C-terminus of PR may be responsible for the inactivity of RU486. Consequently, removal of this sequence would enable RU486 to become an agonist.

EXAMPLE 13

Hormone Binding Analysis

FIG. 4 shows the transcriptional activity and hormone binding analysis of wild type and mutant hPR constructs. hPR constructs are reported to the left side together with a schematic representation of the receptor molecules. Yeast cells were grown in the presence of 100 $\mu$M CuSO$_4$. Transcriptional analysis was done as described above. Experiments were done in triplicate and transcriptional activities were normalized with respect to protein. Hormone binding assays were performed in the presence of 20 nM [$^3$H] progesterone or 20 nM [$^3$H] RU486.

A saturation binding analysis of the UP-1 mutant receptor was performed in order to determine if its affinity for RU486 and progesterone was altered. Scatchard analysis of the binding data demonstrated that both the wild type and mutant receptors had a similar affinity for RU486 of 4 and 3 nM, respectively. As seen in FIG. 4, the mutant receptor molecule had lost the ability to bind progesterone. Thus, the amino acid contacts for progesterone and RU486 with hPR are different.

Generation of Deletion Mutants of hPR-B

As shown in FIG. 2B, DNA sequencing revealed that the frameshift mutation in the UP-1 clone created a double mutation in the receptor protein. That is, a modified C-terminal amino acid sequence and a 42 amino acid truncation. In order to identify which mutation was ultimately responsible for the observed phenotype, two new receptor mutants were constructed in vitro: YEphPR-B879, containing a stop codon corresponding to amino acid 880, and YEphPR-B891, containing a stop codon at amino acid 892. Hormone binding data (see FIG. 4) demonstrated that both of these truncated receptors could bind RU486 but not progesterone. When examined in vivo, both mutant receptors activated transcription in the presence of RU486 to levels comparable to those of the mutant UP-1 generated in yeast. As expected, both mutants were inactive in the presence of progesterone. Thus, the observed phenotype was not due to second site mutations in the UP-1 molecule. Also, 12 additional amino acids, from 880 to 891, were not responsible for the mutant activity. In addition, it is clear the C-terminal 42 amino acids are required for progesterone to bind to the receptor while the last 54 amino acids are unnecessary for RU486 binding. Thus, the antagonist is contacting different amino acids in the native receptor molecule and may induce a distinct receptor conformation relative to agonists.

EXAMPLE 14

Steroid Specificity for Activation of Transcription of the UP-1 Mutant

FIG. 5 shows the specificity of the transcriptional activity of the mutant hPR. In panel (A), wild type and UP-1 mutant receptor transcriptional activities were assayed in the presence of different concentrations of progesterone, Ru486, Org31806 and Org31376 as indicated.

Figure 5A:
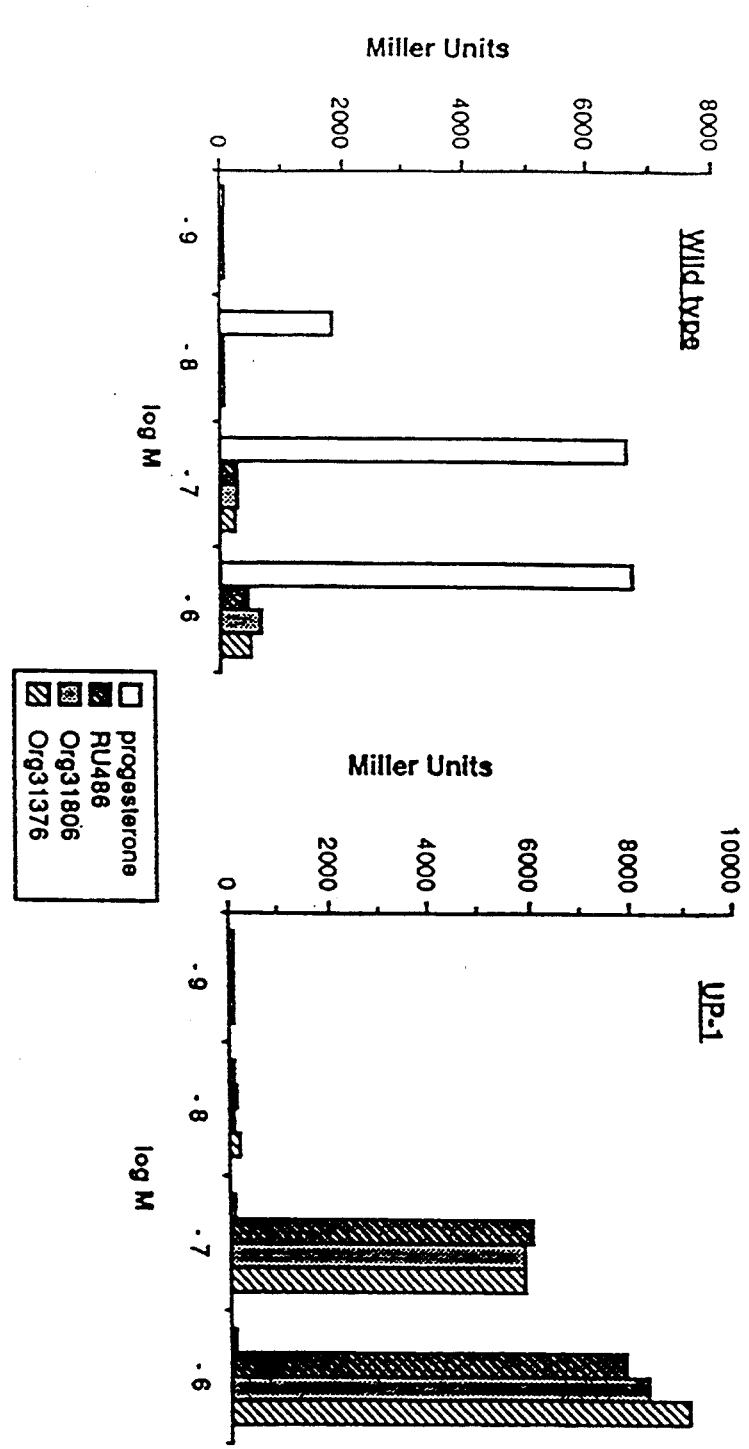
FIGS. 5A and 5B shows the specificity of transcriptional activity of the mutant human progesterone receptor.

A transcription assay was performed using two synthetic antagonists, Org31806 and Org31376, which are potent antiprogestins. As shown in FIG. 5A, the mutant receptor was activated by both of these compounds. The curve of the concentration-dependent activity was similar to that obtained with RU486, suggesting that the affinity of these two antagonists for the mutant receptor is similar to that of RU486. When assayed with the wild type receptor, these compounds had minimal transcriptional activity and behaved like partial agonists (3–10% of progesterone activity) only at concentrations of 1 $\mu$M, as does RU486. Thus, the inhibitory effect of the C-terminus of hPR extends to other receptor antagonists.

Figure 5B:
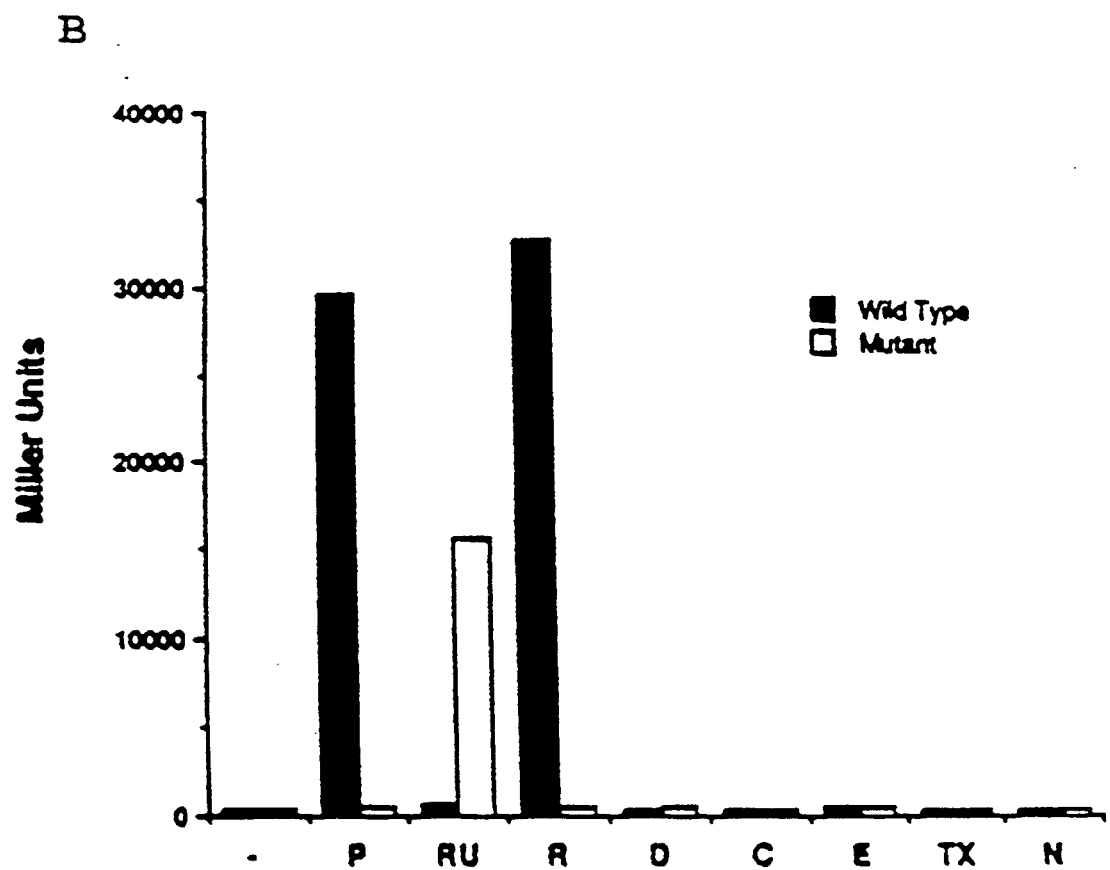

In panel (B), transcriptional activities of wild type and UP-1 mutant receptors were assayed in the presence of 1 $\mu$M progesterone (P), RU486 (RU), R5020 (R), dexamethasone (D), cortisol (C), estradiol (E), tamoxifen (TX) or nafoxidine (N) (see FIG. 5B). The synthetic agonist R5020 had no effect on the UP-1 mutant, suggesting that agonists, such as progesterone and R5020, require the C-terminus of the native receptor for binding and consequently fail to recognize the truncated UP-1 receptor. Other steroids known to enter yeast cells, such as estradiol, the antiestrogens tamoxifen and nafoxidine, dexamethasone and cortisol, might possibly activate the mutated receptor. All steroids tested were found to be inactive with either the wild type or mutant receptor. Thus, the activation of the mutant receptor is specific to antiprogestins.

EXAMPLE 15

Transcriptional Activity of Mutant Receptors in Mammalian Cells

FIG. 6 shows the transient transfection of mutant hPR into mammalian cells. In panel (A), HeLa cells were transiently transfected with phPR-B and pHPR-B891 receptors together with PRETKCAT receptor plasmid using the polybrene method of transfection as described (Tsai, et al. 1989). Cells were grown with or without 100 nM progesterone or RU486 for 48 hours prior to harvesting CAT assays were performed as described above. In panel (B), CV-1 cells were transiently transfected as in (A).

With reference to FIG. 6, mutant receptor activity was assayed in both human endometrial HeLa cells and monkey kidney CV-1 fibroblasts. A mutant, phPR-891, was constructed by replacing the full-length PR insert of phPR-B vector with the truncated PR cDNA of YEphPR-B891. The resulting receptor mutant, phPR-B891, is a 42 amino acid truncation of hPR-B form. Mutant 891 and wild type receptors were transfected into HeLa cells together with the PRETKCAT reporter plasmid, which contains two copies of a GRE/-PRE element.

Figure 6A:
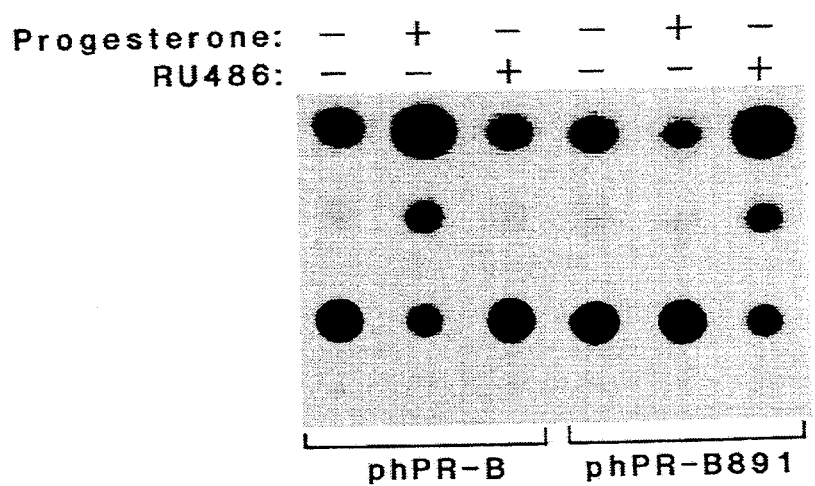
FIGS. 6A and 6B depict the transient transfection of mutant human progesterone human receptor into mammalian cells.

As expected, wild type PR activated transcription of the CAT gene reporter in the presence of $10^{-7}$M progesterone (FIG. 6A). Although basal transcription level was high, a 3- to 4-fold induction of transcription was detected when progesterone was added to the media. In contrast, no induction occurred in the presence of RU486. The high basal level of transcription detected in these experiments may mask or alter an RU486 effect on wild type hPR.

On the other hand, an induction of CAT activity was observed when the 891 mutant was incubated in the presence of $10^{-7}$M RU486 (FIG. 6A). The same concentration of progesterone had no activity.

Figure 6B:
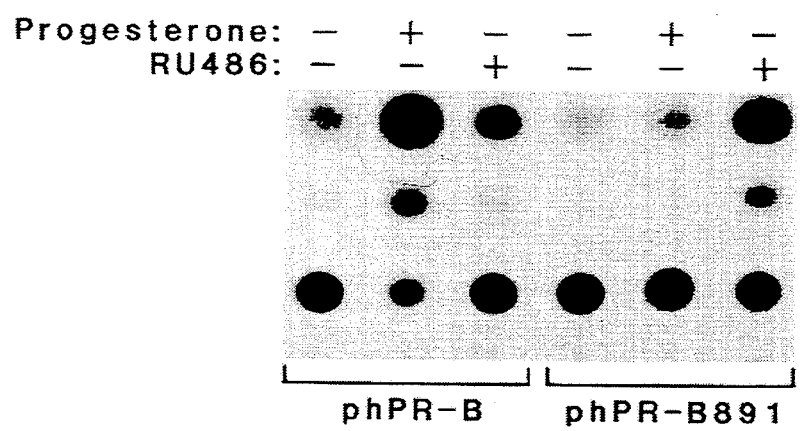

Cell-type specific factors can influence the activity of the transactivating domains of steroid receptors. In order to evaluate this possibility, wild type and mutant receptors were transfected into CV-1 cells. Similar results were obtained, i.e., progesterone activated the wild type receptor while RU486 activated 891 mutant receptor (FIG. 6B).

The protein synthesized from phPR-B891 plasmid was of the correct molecular weight in mammalian cells. The mutant receptor was transfected into COSM6 cells. Western analysis on cell extracts showed that the 891 mutant was synthesized, as expected, as a protein of 109 kDa, which corresponds to a protein 42 amino acids shorter than the wild type hPR. Thus, RU486 acts as an agonist of the truncated B-receptor in a yeast reconstituted system and also in mammalian cells. The mechanism of transactivation does not require the C-terminal tail of the mutant receptor and is conserved between the three species tested.

All patents and publications mentioned in this specification are indicative of the levels of those skilled in the art to which the invention pertains. All patents and publications are herein expressly incorporated by reference.

In conclusion, it is seen that the present invention and the embodiments disclosed herein are well adapted to carry out the objectives and obtain the end set forth in this application. Certain changes can be made in the method and apparatus without parting from the spirit and scope of this invention. It is realized that changes are possible and that it is further intended that each element or step presided in any of the filing claims is to be understood as to referring to all equivalent elements or steps for accomplishing the essentially the same results in substantially the same or equivalent manner. It is intended to cover the invention broadly in whatever form its principles may be utilized. The present invention, therefore, is well adapted to carry out the objects and obtain the ends and advantages mentioned, as well as others inherent therein.

What is claimed is:

1. A mutated progesterone receptor protein, wherein said receptor protein is capable of distinguishing a hormone antagonist from an agonist, wherein said protein is mutated by deletion of about 42 to about 54 carboxyl terminal amino acids.

2. A plasmid containing DNA encoding the mutated progesterone receptor protein of claim 1.

3. The plasmid of claim 2, designated UP-1.

4. A transfected cell containing the plasmid of claim 3.

5. A transformed cell line containing the plasmid of claim 3.

6. The plasmid of claim 2, wherein said plasmid is selected from the group consisting of YEphPR-A879, YEphPR-A891, YEphPR-B891, YEphPR-B879, phPR-A879, phPR-A891, phPR-B879 and phPR-B891.

7. A transfected cell containing the plasmid of claim 2.

8. The transfected cell of claim 7, wherein said cell is selected from the group consisting of yeast, mammalian and insect cells.

9. The transfected cell of claim 8, wherein said yeast is *Saccharomyces cerevisiae*.

10. The transfected cell of claim 8, wherein said mammalian cell is selected from the group consisting of HeLa, CV-1, COSM6, HepG2, CHO and Ros 17.2.

11. The transfected cell of claim 8, wherein said insect cell is selected from the group consisting of SF9, drosophila, butterfly and bee.

12. A transformed cell line containing the plasmid of claim 2.

13. A method of determining antagonist activity of a compound for a progesterone receptor, comprising the steps of:
   contacting said compound with a transfected cell of claim 7; and
   measuring transcription levels induced by said compound.

14. A method of determining agonist activity of a compound for a progesterone receptor comprising the steps of:
   contacting said compound with transfected cells of claim 7; and
   measuring transcription levels induced by said compound.

15. A method of determining agonistic activity of a compound for a progesterone receptor, comprising the steps of
   contacting a compound with the transfected cells of claim 4; and
   measuring transcription levels induced by said compound.

16. A method of determining agonistic activity of a compound for a progesterone receptor, comprising the steps of:

contacting a compound with the transformed cells of claim 12; and measuring transcription levels induced by said compound.

17. A method of determining agonistic activity of a compound for a progesterone receptor, comprising the steps of:

contacting a compound with the transformed cells of claim 5; and measuring transcription levels induced by said compound.

* * * * *